United States Patent
Guillen

(10) Patent No.: US 7,295,124 B2
(45) Date of Patent: Nov. 13, 2007

(54) REFLEX TESTER AND METHOD FOR MEASUREMENT

(76) Inventor: Diego Guillen, 100 N. Barranca Ave., West Covina, CA (US) 91791

( * ) Notice: Subject to any disclaimer, the term of this patent is extended or adjusted under 35 U.S.C. 154(b) by 142 days.

(21) Appl. No.: 11/067,462

(22) Filed: Feb. 25, 2005

(65) Prior Publication Data

US 2006/0195018 A1    Aug. 31, 2006

(51) Int. Cl.
 *A61B 5/11* (2006.01)
 *A61B 5/103* (2006.01)

(52) U.S. Cl. .............. 340/576; 340/539.12; 340/573.1; 600/595; 600/587; 600/558; 434/64; 434/236

(58) Field of Classification Search ................ 600/587, 600/595; 434/64; 340/576, 539.12, 573.1
See application file for complete search history.

(56) References Cited

U.S. PATENT DOCUMENTS

| | | | |
|---|---|---|---|
| 2,273,091 A * | 2/1942 | De Silva ..................... 434/64 |
| 3,233,341 A | 2/1966 | Exton | |
| 3,698,385 A | 10/1972 | Brown | |
| 4,063,807 A | 12/1977 | Gelius et al. | |
| 4,166,452 A * | 9/1979 | Generales, Jr. ............. 600/554 |
| 4,261,563 A | 4/1981 | Goldfarb | |
| 4,589,849 A | 5/1986 | Casey | |
| 4,763,898 A | 8/1988 | Hemmann | |
| 4,824,237 A | 4/1989 | Ratner et al. | |
| 4,852,570 A * | 8/1989 | Levine ....................... 600/301 |
| 5,079,726 A | 1/1992 | Keller | |
| 5,203,346 A | 4/1993 | Fuhr | |
| 5,221,243 A | 6/1993 | Walker | |
| 5,289,389 A | 2/1994 | Keller | |
| 5,490,517 A | 2/1996 | Whitman et al. | |
| 5,520,393 A | 5/1996 | Rickey | |
| 5,803,745 A | 9/1998 | Kozak et al. | |
| 5,812,239 A | 9/1998 | Eger | |
| 5,882,011 A | 3/1999 | Praria | |
| 6,004,281 A * | 12/1999 | Harbin et al. ............... 600/595 |
| 6,066,105 A | 5/2000 | Guillen | |
| 6,267,733 B1 * | 7/2001 | Peterson et al. ............ 600/587 |
| 6,371,931 B1 * | 4/2002 | Guillen ....................... 600/595 |
| 6,416,485 B1 * | 7/2002 | Rovetta et al. .............. 600/595 |
| 6,565,359 B2 * | 5/2003 | Calhoun et al. ............ 434/236 |
| 6,702,756 B2 * | 3/2004 | Brown ....................... 600/558 |
| 6,702,757 B2 * | 3/2004 | Fukushima et al. ......... 600/558 |
| 2002/0011250 A1 * | 1/2002 | Stewart et al. .............. 128/898 |
| 2004/0177686 A1 * | 9/2004 | Johansson ................ 73/379.01 |

FOREIGN PATENT DOCUMENTS

WO    01/89376    11/2001

OTHER PUBLICATIONS

Wolf et al., "Assessing Wolf motor function test as outcome measure for research in patients after stroke" *Stroke* 32(7):1635-9, 2001.

* cited by examiner

*Primary Examiner*—Jeffery Hofsass
*Assistant Examiner*—Anne V. Lai
(74) *Attorney, Agent, or Firm*—Fish & Richardson P.C.; Fred C. Hernandez

(57) ABSTRACT

A response measuring system for measuring the time required for a user or subject to respond to a prompting event includes a controller or computer connected to a plurality of annunciator driving outputs and a plurality of sensor input receivers. Methods of using the response measuring system in diagnoses and prognosis of injury, disease, and disorders.

20 Claims, 8 Drawing Sheets

US 7,295,124 B2

REFLEX TESTER AND METHOD FOR MEASUREMENT

TECHNICAL FIELD

The disclosure relates to a system and method for testing individual cognitive ability in combination with reflexes, dexterity, reaction time and range of motion/mobility, and further relates to a system for objective, automated testing and objective data recording for use by any of a variety of individuals, including, for example, physicians, neurologists, physical therapists, trainers, and technicians.

BACKGROUND

A number of reaction testing devices have been employed in games for amusement and for diagnostic testing of physical acuity, reaction time and dexterity.

NASA has used reaction testing for measurement of "simple" and "disjunctive" responses to light stimuli, as disclosed in U.S. Pat. No. 3,698,385, to Low et al., in which a base includes two parallel finger grooves with sensors. The subject observes "ready", "left" and "right" light indicators and responds by placing a finger in a selected groove where the finger's presence is sensed, a test which provides a raw count of the number of clock cycles required for a given individual to correctly respond to the "left" or "right" light stimulus.

Others have used systems with similar electrical circuits to provide specific kinds of occupational training (see, e.g., U.S. Pat. No. 4,589,849 to Casey and U.S. Pat. No. 5,289,389 to Keller), and dancing (as shown in U.S. Pat. No. 3,233,341). But none of these devices is readily used in a comprehensive regimen of physical therapy for testing a subject's cognitive ability, reflexes and/or range of motion and mobility.

Neurological and musculoskeletal injury resulting from work related injuries and/or other accidents often affects a person's motor function. Upper extremity impairments after neurological and/or musculoskeletal injury typically include weakness, tone abnormalities, sensory and perceptual difficulties, incoordination, and general motor control difficulties. Objective measures of cognitive ability, mobility and motor function after injury are critical for rehabilitative treatment planning and compensation evaluation. It is also critical to be able to monitor an individual's rehabilitative progress, as well as the effects of drugs/medications on the individual.

A number of theories suggest that movement is the result of complex interactions between the individual, the task and the environment (Bernstein, "The coordination and regulation of movement." London: Pergamon, 1967; Shumway-Cook et al., "Motor Control: Theory and Practical Applications." Philadelphia, Pa.: Lipponcott; 2001; Wolf et al., *Stoke* 32 (7):1635-9, 2001). It is thought that the process includes first perceiving and understanding a particular task or goal-directed movement, developing a motor plan based upon the environment, and generating a motor response in order to complete the task.

A physician, neurologist, physical therapist, trainer, or occupational therapist requires a way to provide a meaningful, objective examination of a subject's capabilities, to determine how the subject's capabilities are changing as therapy progresses, and to determine the changes that medications are having on the subject.

SUMMARY

There are now described devices and methods for testing, ascertaining, and otherwise evaluating the cognitive ability and overall physical ability of an individual. In one aspect, there is described a response measuring system for measuring the time required for a user to respond to an event, comprising: a computer; a display screen; a seat; a steering device; one or more foot pedals; a plurality of sensor input receivers associated with the steering device and the one or more foot pedals for sensing a change in position of the steering device and one or more foot pedals; and a computer readable medium comprising instructions to cause the display of a display scenario on the display screen, the display scenario comprising annunciator outputs; a timer responsive to said annunciator outputs and the plurality of sensor input receivers, the timer being configured to measure time elapsed between actuation of an annunciator output and generation of a sensor input signal to generate a response time signal from an elapsed time; and a memory device to store the elapsed time.

In another aspect, there is described a reflex response device for diagnosing a neurological and/or musculoskeletal disease or disorder comprising: a controller comprising: a plurality of annunciator driving outputs; a plurality of sensor input receivers; a timer responsive to the said annunciator driving outputs and the sensor input receivers; and a memory responsive to said sensor input receivers; a plurality of annunciators responsive to said controller annunciator driving outputs; a plurality of sensors, each individually connected to a plurality of sensor input signal generators each generating a sensor input signal transmitted to said plurality sensor input receiver; wherein each of the plurality of annunciators are positioned to be perceivable by the user and wherein each of the sensors are operable by the user; said controller timer being configured to measure time elapsed between actuation of an annunciator of the plurality of annunciators and generation of a corresponding input from the plurality of sensors to generate an elapsed time; wherein the memory is configured to store the elapsed time; a database comprising user specific information; and a computer program on computer readable medium comprising instructions to cause the computer to acquire an elapsed time and to associate the elapsed time with the user specific information to diagnose a neurological and/or a musculoskeletal disease or disorder based upon the elapsed time.

The details of one or more embodiments of the disclosure are set forth in the accompanying drawings and the description below. Other features, objects, and advantages of the disclosure will be apparent from the description and drawings, and from the claims.

DESCRIPTION OF DRAWINGS

Like reference symbols in the various drawings indicate like elements.

DETAILED DESCRIPTION

Figure 1:
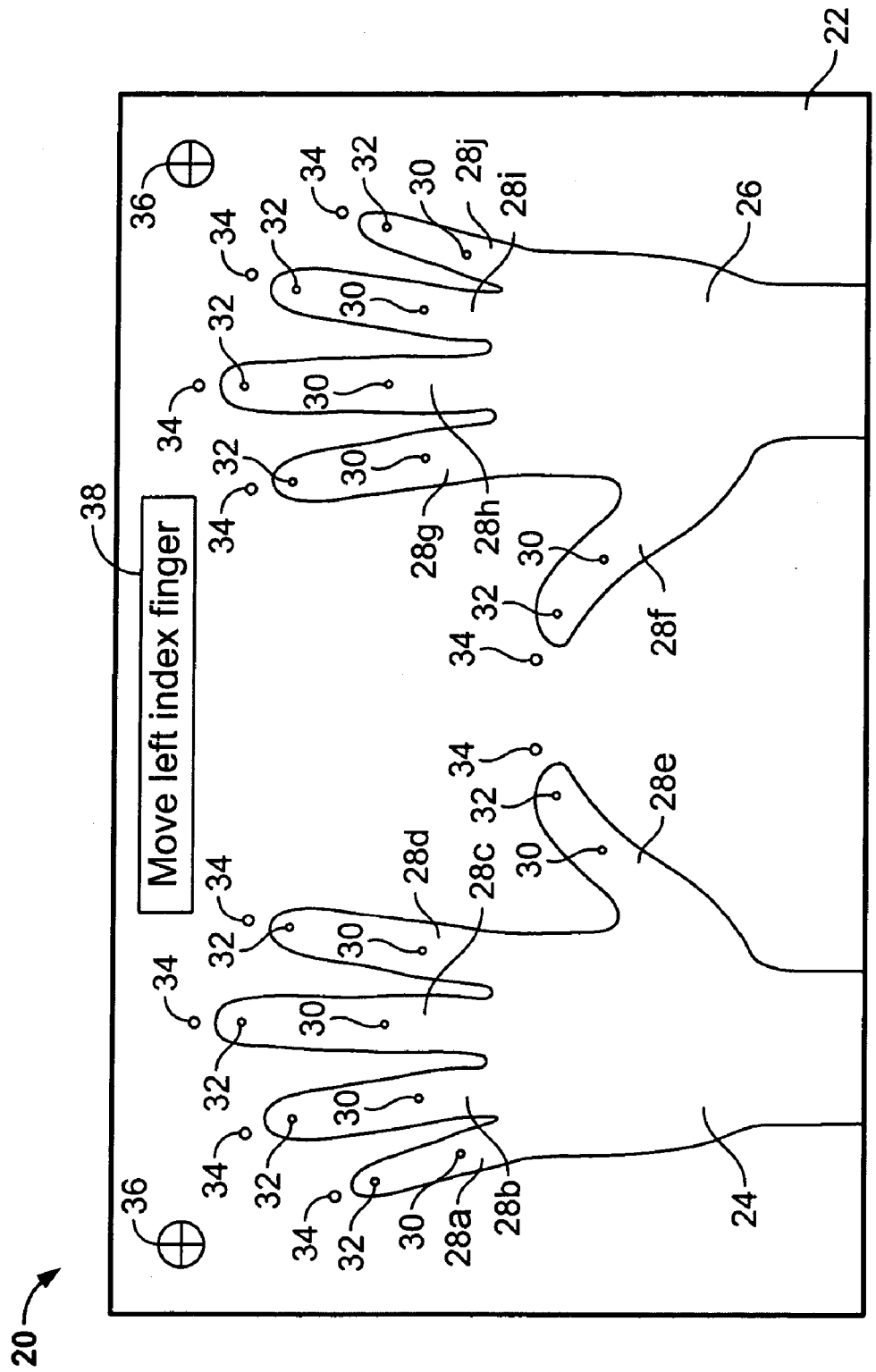
FIG. 1 depicts a response measuring system for hand movement including a first area adapted to receive the left hand and a second area adapted to receive the right hand.

There are now described devices and methods for testing, ascertaining, and otherwise evaluating the cognitive ability and overall physical ability of an individual. The term "physical ability" includes any of a wide variety of physical attributes, including for example, but not limited to, reflexes, reaction time, range of motion, eye-hand coordination, depth perception, peripheral vision, mobility, dexterity, etc. of an individual.

For example, a person's physical ability can relate to the person's range of motion and movement, how quickly the person can move back and forth over a range of motion, how quickly the person can react, the strength of a person and the strength distribution over a range of limbs or digits, etc. It should be appreciated that the term "physical ability" is not limited to the foregoing attributes, but can rather include any physical attribute.

As described in more detail below, the disclosed devices and methods provide objective data indicative of both the cognitive ability and physical ability of the individual. Applicant has observed that it is advantageous to ascertain both the cognitive ability and physical ability of an individual, as well as the interaction of cognitive and physical ability. In this regard, there are disclosed herein devices and methods that require an individual to perform both cognitive and physical tasks and combinations thereof to yield objective data that is indicative of the individual's capabilities (both cognitive and physical).

As described more fully below, the objective data can be used in a variety of manners. For example, the data can be used to provide an initial, objective "snapshot" of the individual's capabilities at a certain time. The data can also be gathered over time to arrive at a baseline that can be compared with subsequent data to determine whether the individual's capabilities are progressing or being affected by some factor, such as medication, drugs, or other type of treatment or rehabilitation. It should be appreciated that the uses of the objective data can vary widely and that the examples described herein are not limiting.

As mentioned, the disclosed devices and methods require the individual to perform tasks that yield data reflective of both cognitive and physical ability and combinations thereof. Regarding cognitive ability, the tasks require the individual to exercise mental awareness of his/her surroundings and to perform evaluative and judgmental thought processes that are generally cognitive in nature. The cognitive tasks are performed in combination with tasks that are generally physical in nature. Such physical tasks can involve hand-eye coordination, reflexes, reaction time, depth perception, range of motion and mobility, dexterity, strength, etc. It should be appreciated that the aforementioned cognitive and physical tasks are merely exemplary and such cognitive and physical tasks can vary widely.

In accordance with the disclosure, a response and cognitive ability measuring system for measuring the time required for a subject to respond to an event including a plurality of tasks, comprises a computer connected to a plurality of annunciator outputs and a plurality of sensors. The computer also comprises a timer that measures the response time between an annunciator output and a sensor input as well as the time between one or more sensor inputs. The computer further comprises a computer memory for storing response times. The computer may also comprise a communications medium to allow for communication of data and information to a central location via the internet or direct connections.

The annunciator comprises a stimulator that provides any physical stimuli that is perceivable by a subject (i.e., sight, hearing, taste, smell, touch) and indicate an activity to be carried out, wherein the activity involves both physical and cognitive actions. For example, an annunciator can include a visible stimulus such as display of directions or lights, tactile stimulus (e.g., vibrations), and/or an auditory stimulus (e.g., sound or verbal commands).

The annunciator provides stimulus comprising a cue or prompt to the user that induces a response by the user. The sensors, in general terms, sense the user's response. A timer is used to measure the interval required from the point in time of receiving a stimulus and the point in time whereby a user provides the required response (including a total time and/or times for fragments of the overall response process). In this manner, objective data, such as reaction time, can be obtained. The system includes a support member or housing for carrying and positioning the sensors and annunciators for a given test.

In one embodiment, the reflex measuring system of the disclosure comprises a housing including a first area adapted to receive a hand and, optionally, a second area adapted to receive the opposite hand; subareas may be designated for each finger. The finger subareas in the first and second areas comprise an annunciator, and a sensor. The annunciator can be, for example, a vibrotactile stimulator, and the sensor can be a button actuated microswitch (or reset button).

In another aspect, the annunciator is a light emitting diode just beyond each finger subarea, or other light source visibly positioned for indicating which finger is to be flexed and depressed in responding to a light stimulus.

In one embodiment, each finger may also be located in a fingerstall comprising pressure sensors capable of measuring the amount of pressure applied to a sensor to measure the strength of one or more fingers. In yet another aspect, the annunciator may be an auditory stimuli, such as verbal directions indicating a finger to be flexed.

During use, a stimulus comprising an actuation of a selected annunciator (e.g., a selected LED light source, actuation of the selected vibrotactile stimulator and/or an auditory stimulus) is provided to the subject. It should be appreciated that certain examples, such as an LED light source are provided herein but that the devices and methods are not limited to such examples. Once the subject sees, feels or hears the annunciator (e.g., sees the LED or feels the vibrotactile stimulator), the user immediately contacts the appropriate sensor (e.g., depresses the appropriate reset button). The computer then senses and determines the amount of time elapsed between activation of the annunciator and contact with the appropriate sensor (i.e., the subject's correct response).

A test pattern or an exercise pattern may be performed by the system. The subject can be tested to determine whether a response is faster for what is seen (e.g., the LED), what is felt (e.g., the vibrotactile stimulator) or what is heard (e.g. auditory stimuli). The timer (or clock) is activated immediately upon lighting of the LED indicator, activating of the finger vibrotactile stimulator, and/or at the beginning or completion of the auditory/text stimuli and the timer stops upon pressing of the indicated/appropriate reset button.

After completion of the test, the reaction time data measurements may be plotted or reported to show the results using the computer display or an attached printer. In some instances the data may be transmitted to a remote location by a communication device.

Referring now to FIG. 1 of the accompanying drawings, a reflex tester or response time measuring system 20 includes a housing 22 having an upper surface including a left hand area 24 and a right hand area 26, adapted to receive the user's left and right hands, respectively. Housing 22 may optionally include only a single hand receiving area (e.g., 24 or 26) (or individual sensors), in a range of sizes for users of differing hand size or shape, or in a range of finger/thumb orientations. Alternatively, each finger may be located in stalls comprising individual sensor appenditures (e.g., fingerstall devices)

Finger subareas 28a-28j are designated for each finger and thumb in hand areas 24 and 26. The finger subareas 28a-28e in the first, left hand area 24 and finger subareas 28f-28j in second, right hand area 26 can include a vibrotactile stimulator 30 (located within the housing at approximately the mid-point of each finger subarea 28a-28j), a button actuated microswitch (or reset button) 32 located under the finger-pad area near the finger subarea distal end and, typically, just beyond each finger subarea 28a-28j. A light emitting diode (LED) 34 or other light source may be present and visibly positioned for indicating which finger is to be flexed in responding to the selected stimulus.

The stimulus comprises actuation of the selected LED light source 34, actuation of the selected vibrotactile stimulator 30, or both. Once the user sees actuation of a selected LED 34 (e.g., for finger subarea 28e under the left thumb) or feels the vibrotactile stimulator 30 actuated, the user immediately depresses the appropriate reset button 32. A computer or controller then senses the amount of time elapsed between actuation of the selected light indicator 34 or vibrotactile annunciator 30 and sensing of depression of the button 32 signaling the user's correct response. A test pattern (for recording) or an exercise pattern (not recorded) may be performed and testing can be divided into two areas.

The subject can be tested to determine whether response is faster for what is seen (e.g., the LED 34) or what is felt (e.g., the vibrotactile stimulator 30). Alternative speakers 36, may give audio commands such as "move left index finger" or display 38 may give visual instructions. The controller timer (or clock) is activated immediately upon lighting of the LED indicator 34 or activating of the finger vibrotactile stimulator 30 and is stopped upon pressing of the indicated, corresponding reset button 32.

After completion of the test, the reaction time and/or strength measurements may be plotted to show the results using the computer display or an attached printer. The type of "strength measurements" can vary widely. The strength measurements can include measurements where body parts are at rest and in action, such as during gripping, pinching, grabbing, etc. With regard to actions such as gripping or pinching, the strength measurements include measurements of force distribution, such as the force distribution among fingers of a hand or among different hands.

For example, if "pinching strength" is being measured between two fingers, the strength measurements desirably reflect which finger is exerting more force and the amount of force. It should be appreciated that the type of strength measurement can vary and is not limited to those described herein.

In another aspect, the data can be stored in a database associate with a particular subject's information (e.g. medical information). In yet another embodiment, the data is communicated to a central location over a communications network.

In general, response measuring system 20 measures the time required for a subject (e.g., a patient) to respond to a prompting event and includes a controller or computer connected to a plurality of annunciator driving outputs and a plurality of sensor input receivers. The controller also includes a timer responsive to both annunciator driving outputs and sensor input receivers; a controller memory stores response times.

The annunciators can be lights, sounds, or tactile vibrating stimulators for cuing or prompting the user into responding. The sensors sense the user's response and the timer is used to measure the interval required for the user to respond. The system includes a support member (e.g., a housing 22) for carrying and positioning the sensors and annunciators for a given experiment.

Peg Board System

In another embodiment, described further below with reference to FIGS. 2A and 2B, a panel includes a plurality of pegs of various readily distinguishable sizes and shapes arranged in a plurality of columns or rows (in the vertical, horizontal, or diagonal) to the left and right of a central area. In one aspect, the panel, comprising the pegs, can be tilted between horizontal and vertical and various intermediates there between. For example, the panel can lie in a horizontal orientation or can be adjustably tilted to a selected angle (e.g. between 0° and 90°). In addition, the height of the panel can vary (e.g. from about 28" to about 42" above the floor). The aforementioned dimensions are merely exemplary and are not limiting.

The number of columns/rows and pegs per column/row are selectable to satisfy the requirements of a given application. The pegs can be color coded. The number of shapes and columns/rows can be varied as needed. Some examples are now provided, although it should be appreciated that actual embodiments can vary. For example, the number of columns/rows can be from 1-9 (or more) on the left, 1-9 (or more) in the center and 1-9 (or more) on the right. The number of pegs can vary from as few as 1 to as many as 28 or more. Each peg will typically have a distinctive shape; the shape being attached to handles that are about ½ inch to 1 inch in diameter and about 3" high.

In one aspect, on the left, first, second and third columns each contain seven shapes stored within vertically arrayed pockets (e.g., apertures). The shapes can be, for example, a small circle, a large circle, a rectangle, a diamond, a triangle, a square, and a star, although it should be appreciated that the shapes can vary.

Each shape is a "peg" or test object, which can be removed from a holder or pocket in a selected column and placed in a specified corresponding receiving aperture (having the same shape and, typically, color) within the central area. Each aperture includes an annunciator (e.g., an LED) and a sensor to detect the presence of a peg or test object. Typically, three columns are arranged to one side (e.g., the left or right) of the central area with three columns arranged to the opposing side (e.g., the right or left), thereby allowing the subject to demonstrate a range of motion in reaching outwardly, to opposing sides (e.g., left or right), to the outer columns, as well as reaching up or down, within a column. The range of motion includes returning back to the original position.

In use, the selected peg or target object can be illuminated using an LED annunciator, thereby starting the timer. The subject grasps the target object and removes it from the target object holder in a starting column, moves the target object and then inserts it into a corresponding receiving aperture in another part of the board, such as the central area or on the opposite side of the board. The process results in both a triggering of a sensor in the holder having the test object or peg and a triggering of a sensor in the aperture, designated to receive the test object or peg.

The test generally starts as follows. The subject first presses an appropriate button or otherwise actuates some actuator, such as a home/start/stop button. The button is positioned at a location that is advantageous for testing purposes. For example, in testing the left side of the body, the button can be located to the right of the subject's body thereby requiring the subject to reach to the right.

Once the button is pressed, a first timer is initiated to measure the subject's cognitive ability. The timer is used to measure how long it takes for the subject to (1) recognize a command (either through seeing, hearing, reading, or otherwise observing the command); (2) understand the command; (3) put together an action plan; and (4) send a signal to the body to execute the command. In this regard, the subject is required to use his/her cognitive abilities in that the person must think, develop an action plan, and act on the action plan. Thus, the first timer measures how long it takes for the person to perform a cognitive task.

The command may comprise, for example, an instruction for the subject to move a peg from one location to another location. Once the user acts on the command (such as by selecting the correct peg), the first timer is turned off, thereby providing the amount of time that it took for the person to perform the cognitive portion of the test (i.e., developing and acting on the action plan).

The system has access to known data (such as the distance between the button and the given shape) and measured data (such as the amount of time to select the correct shape). The system can then measure the elapsed time to complete the task and calculate the acceleration and speed of movement of the subject. This provides an objective measurement of the user's cognitive ability.

A second timer is turned on when the correct peg is selected and turned off when the peg is positioned in the correct destination. As discussed, the distance that the peg was moved is known, as well as the amount of time to move the peg across the distance. Thus, objective measurements for moving the peg can be calculated. The second timer is used to measure how long it takes for the subject to perform a physical task.

A third timer is turned on when the peg is placed in the correct location and then-turned off once the appropriate button is pressed, thereby completing the task. An objective measurement of time and speed for completing the task is thereby obtained. Thus, the first timer provides a measurement of cognitive ability, the second time provides a measurement of the user's physical ability (such as movement speed) and the third timer provides a measurement of time to complete the task.

Thus, the timer measures the time required for the subject to complete the operation and/or sub-parts of the process. For example, the system may measure (i) the time between activation of the annunciator until the sensor in the aperture designated to receive the test object is triggered, (ii) from the time the holder containing the test object or peg is triggered until the time that the sensor in the aperture designated to receive the peg is triggered, and/or (iii) from the time the annunciator is activated until the receiving aperture sensor is triggered.

In another aspect, the timing measurement includes the time from the user activating a start button upon hearing the instructions and then returning to the same or similarly located button and activating the button as a "stop" button. For example, upon hearing or seeing the instructions, the user must process the instructions cognitively. This cognitive response time is a measurement from the time the instructions are completed until the time the user activates a "start" button.

In one aspect, the peg board includes an annunciator comprising an instruction display for displaying a message. For example, a message "move star from column 2 to lighted star position in center bank" can be displayed. (This is merely an example and is not limiting.) A display may also show an image or diagram of the movement to be performed. For example, the display may show a picture of a star in the left bank with a diagrammatic arrow to a position with a star on the center bank. Such schematic displays allow deaf or illiterate users to take part in the measurements.

This annunciator may be accompanied by auditory stimuli (i.e. a similar verbal command). The time required for a subject to perform this operation and/or a part of the operation is measured and recorded. In one aspect of the disclosure, the system measures and records how long the message was displayed and/or the time used for the user to return an appendage (e.g., a hand or finger) back to the starting position. In one embodiment, results for a minimum of three trials are recorded, although it should be appreciated that the number of trials can vary. The system also has the capability of running a test pattern and a random practice or exercise pattern.

Figure 2A:
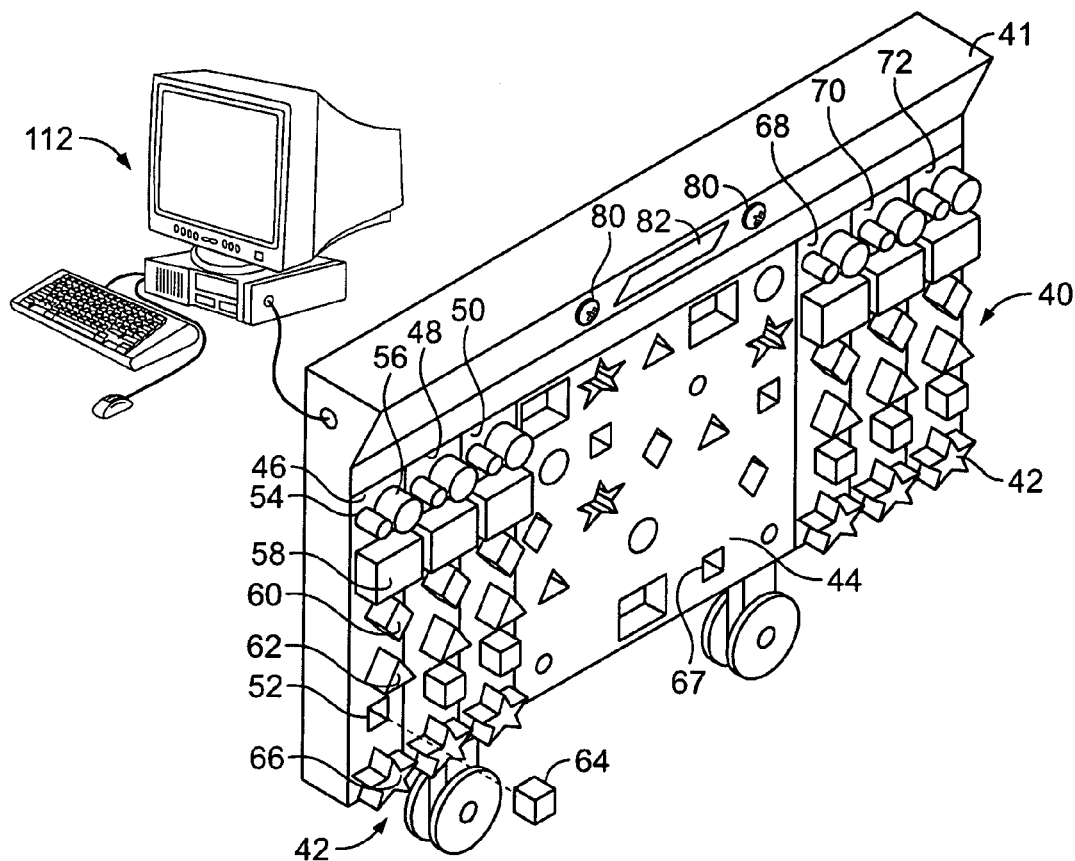
FIGS. 2A-B is a perspective illustration of a reflex measuring system including a plurality of test objects.
Figure 2B:
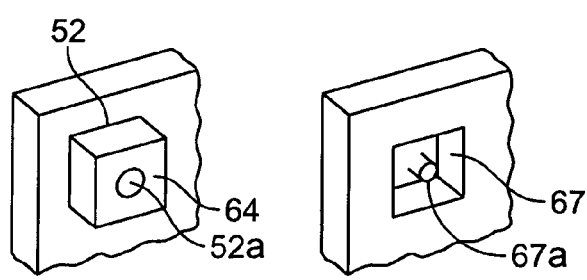

FIG. 2A depicts a reflex measuring system 40 including a vertically oriented panel housing 41 with plurality of test objects or pegs 42 of various readily distinguishable shapes and sizes arranged in a plurality of columns to the left and right of a central area 44. Alternatively, panel housing 41 can lie in a horizontal orientation or can be adjustably tilted to a selected angle (e.g., 0-90°); panel housing 41 is height adjustable and can be raised a selected distance from the floor (e.g. 28" to 42") and locked in a selected angular orientation and at a selected height. The number of columns and pegs per column are selectable to satisfy the requirements of a given application, and the pegs 42 can be color coded. The dimensions and orientation of the panel can vary.

The left, first column 46, second column 48 and third column 50 in the depicted configuration of FIG. 2, each contain seven shaped pegs 42 stored within vertically arrayed pockets 52. Each column (e.g., 46, 48, 50) includes pegs in the following exemplary shapes: a small circle peg 54, a large circle peg 56, a rectangle peg 58, a diamond peg 60, a triangle peg 62, a square peg 64 and a star peg 66. It should be appreciated that the shapes can vary. In another aspect, all the pegs may be the same size.

The peg shapes and quantities shown in FIG. 2 are exemplary only; many other shapes could be used and more or fewer shapes could be employed, further, in alternative embodiments, the shapes can be of uniform color. The invention may also include a rearrangeable or replaceable peg array that allows for changing the peg display when desired.

In the embodiment of FIG. 2A, each peg 42 can be removed from a holder or pocket 52 in selected one of the columns (e.g., square peg 64) and placed in a corresponding receiving aperture (e.g., square aperture 67, see FIG. 2B) within the central area 44; corresponding apertures within the central area 44 have the same cross-sectional shape and, typically, color as the selected peg and are sized to slidably receive the corresponding peg. Each receiving aperture (e.g., square aperture 67) includes a sensor 67a (see, e.g., FIG. 2B) to detect the presence of the peg, once inserted, and a source of illumination selectively enabled and responsive to controller 112.

In an exemplary embodiment, three columns 46, 48, 50 are arranged to the left of the central area 44 with three columns 68, 70, 72 arranged to the right, thereby allowing the user to demonstrate a range of motion in reaching outwardly, left or right, to the outer columns 46, 72, diagonally, as well as reaching up or down, within a column (for a selected panel housing height) and vice-versa. In one aspect, the one aperture to the next is slightly rotated with respect to another aperture of similar size and shape. In this way, a subject must rotate the peg shape by a desired degree in order to slidably insert the peg into the aperture to test the subject's fine motor skills. Such action utilizes various dexterous movements thereby testing the ability of the subject muscles, fine motor skills and coordination. The pegs 42 can be at least partially translucent to pass illumination provided from within pocket 52; an LED 52a in each pocket 52 is selectively enabled and responsive to controller 112.

In use, an annunciator (e.g. 52a, 80, or 82) is used to identify a selected test object (e.g., a rectangle peg 58). The annunciator can be an illuminator 52a, an auditory sound 80, a tactile stimulator, a light-to-light instructional display, a pictoral/schematic display, or any combination thereof. For example, the test object can be identified by using an LED annunciator situated within the pockets 52 (the LEDs are as described in the first embodiment, above), thereby starting a timer in controller or computer 112.

The subject then grasps, for example, square peg 64 and removes it from the peg's holder in the starting column (e.g., square pocket 52), moves the peg 64 and then inserts it into a corresponding aperture e.g., 67 designed to receive that peg in central area 44, thereby triggering a sensor 67a in the aperture 67. The timer measures the time required for the subject to complete the operation or a part thereof. For example, the system can measure the time between activation of the annunciator and removal of the identified peg as well as the time from the point of removing the peg to inserting the peg into a receiving aperture. The system can also measure the time from activation of the annunciator to placing the peg into a receiving aperture.

Another exercise is performed to measure the time required to move all pegs from one or more side columns (e.g., left side first column 46) into corresponding apertures in central area 44. Alternatively, the exercise can be started with the pegs installed in the apertures of central area 44 and the user is timed while moving all pegs to the appropriate apertures in one or more selected side columns (e.g., columns 48 and 50).

In another aspect, the timing measurement includes the time from the user activating a predetermined actuator (such as a start button), which triggers a set of instructions, and then returning to the same or similarly located button and activating the button as a "stop" button. For example, upon hearing or seeing the instructions, the user must process the instructions cognitively. This cognitive response time is a measurement from the time the instructions are completed until the time the user activates a "start" button.

The peg board can include an annunciator comprising an instruction display 82 for displaying the message "move rectangle from left bank column 1, to lighted rectangle position in center bank" (citing a single example). The time required for the subject to perform this operation is measured and recorded; in addition, the system measures and records how long the message was displayed and the time used for the user to return, for example, the user's hand back to a starting position. Typically, results for a minimum of three trials are recorded, although this can vary. The system also has the capability of running a test pattern and a random practice or exercise pattern.

Hemispherical System

Figure 3A:
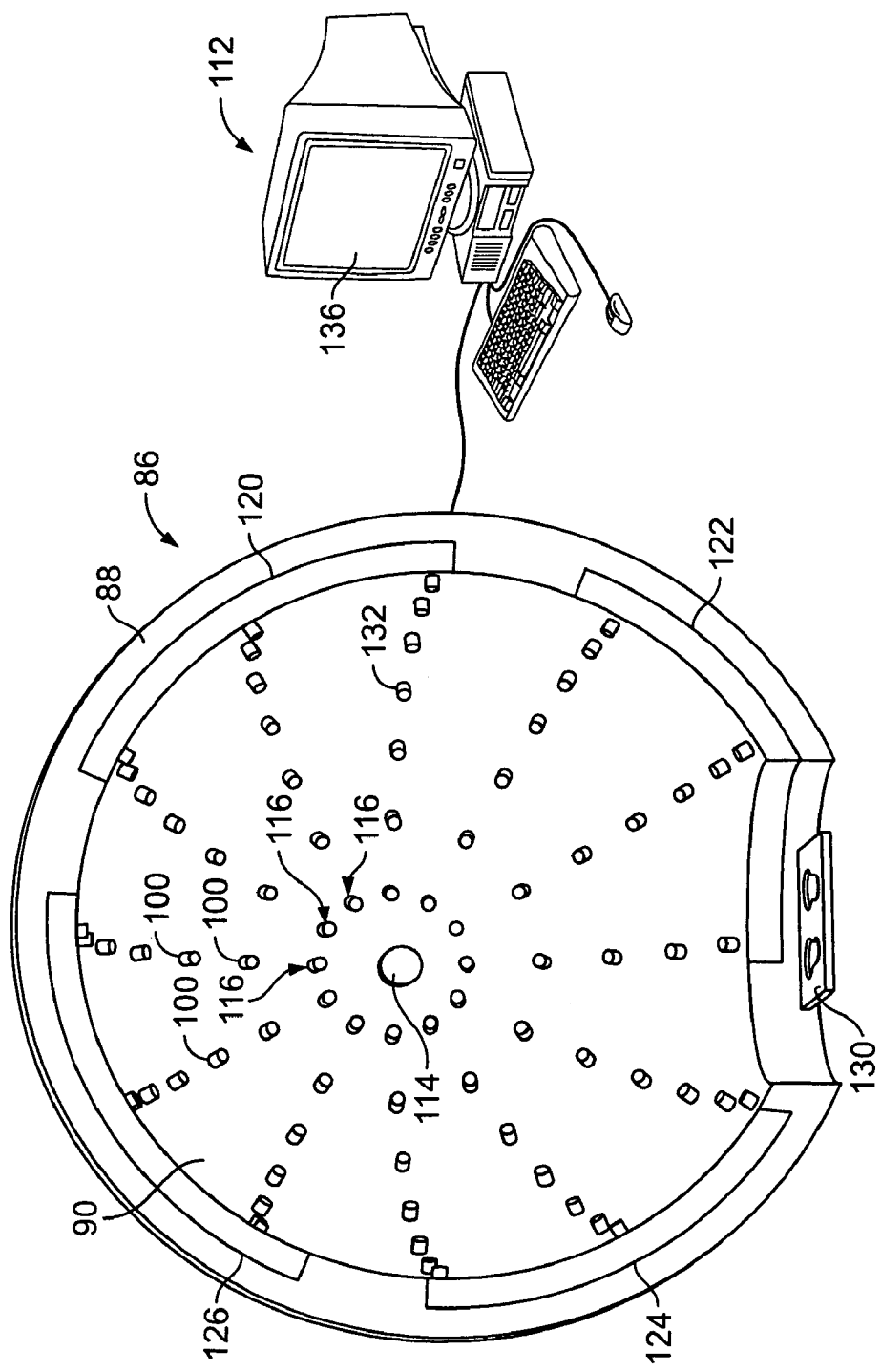
FIG. 3A is a perspective view of a standing hemispherical reflex testing system.
Figure 3B:
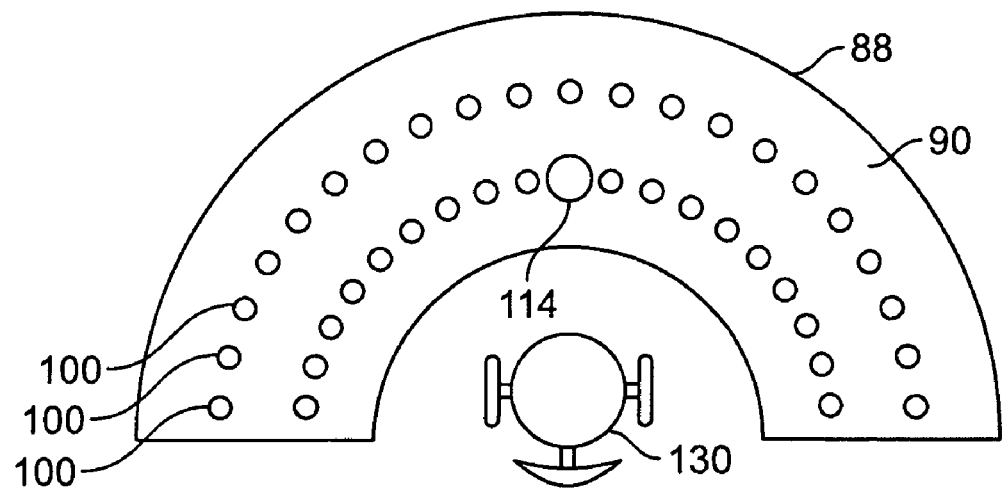
FIG. 3B is a perspective view of a seated hemispherical reflex testing system.
Figure 3C:
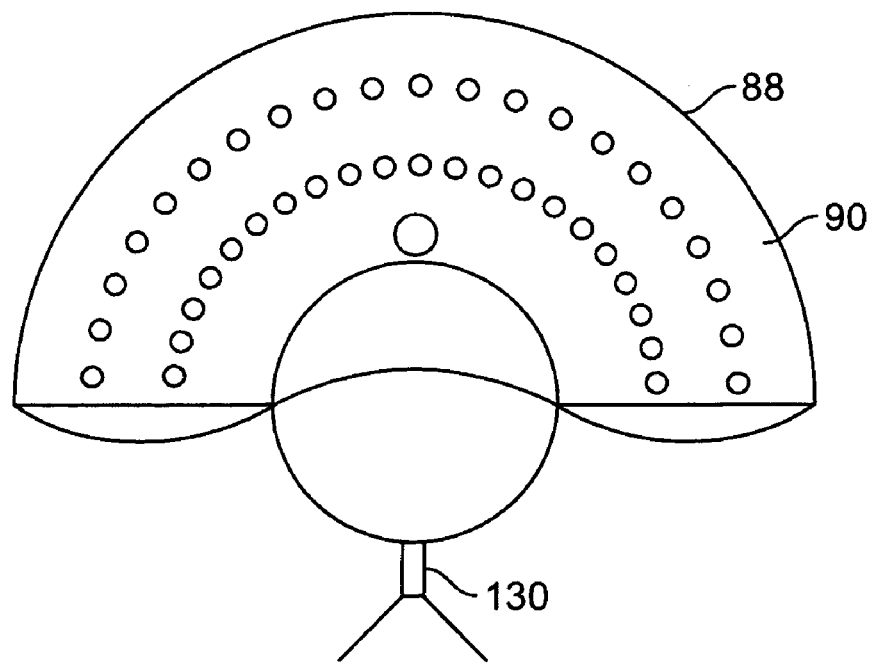
FIG. 3C is another view of a seated hemispherical reflex testing system.

In a third embodiment, described in more detail below with reference to FIGS. 3A-3C, the system comprises a hemispherical system which includes a housing having a substantially hemispherical interior surface comprising small lights and associated buttons (e.g., LED buttons). Each button includes an annunciator light and a sensor microswitch for generating a sensor input signal. Typically, the lighted buttons are arrayed in radial lines within the hemispherical surface. In one aspect of the disclosure, a large, lighted button is disposed approximately at the center of the hemisphere, typically at the intersection of two perpendicular lines bisecting the hemisphere.

In an exemplary embodiment, a first circular array of twelve small, equally spaced lighted buttons encircles the central lighted button at a first radius. The first circular array of lighted buttons corresponds roughly to the positions of the numerals on an analog clock face. Additional circles of lighted buttons can be arranged at increasing radii. For example, six more circles of twelve lighted buttons each are arranged at radii progressively larger than the first radius, thereby providing twelve linear, radially projecting arrays of seven lighted buttons each.

The buttons are spaced evenly in radius to the edge of the hemispherical interior surface. As the radius of the furthest circle of lighted buttons will typically be at the limit of a user's range of motion. For example, if seven or more circles of lighted buttons are provided, greater resolution in characterizing the user's range of motion (and visual acuity) is obtained. It should be appreciated that the configuration and quantity of the buttons can vary.

In an embodiment of the disclosure, the hemisphere is defined in four quadrants, the first quadrant begins at position one and extends through position three (including three radial arrays of small buttons). The second quadrant begins at position four and extends through position six (also including three radial arrays of small buttons). The third quadrant begins at position seven and extends through position nine and the fourth quadrant begins at position ten and extends through position twelve. The four quadrants are arrayed to cover a 360° circle within the hemispherical surface.

In use, a subject stands or sits at approximately the center of the hemisphere (the hemisphere may partially envelop the subject) and places an extremity (e.g., a hand) or an identical central lifted button or touches a central lighted button, thereby activating the system and indicating that the subject is ready to begin, whereupon a test or exercise pattern of light illumination is commenced.

During the test, an annunciator is activated (e.g., one of the smaller lighted buttons at, for example, radial row three, position five is illuminated). The annunciator identifies the position to be touched or action to be taken. For example, where a button is lighted this button becomes an 'object button'; the user undertakes cognitive action by putting together an action plan, sending the signal to the appropriate part of the body, then a physical action to depress the object button thereby triggering a microswitch associated with the button.

The time between the annunciator's activation and each of the individual actions of the subject (e.g., the time between annunciator activation and depression of the object button and then depression of the central button, e.g., a start/stop button) are recorded. Furthermore, individual and total time for action (e.g., from activation of the annunciator to depression of the central button and object button) can also be recorded.

For example, when the fifth button light located on row 3 is lit, a computer immediately actuates (e.g., turns on) a first timer, thus measuring the time required for the user to press the lit object button located on row 3 position 5. Immediately upon pressing the lit button on row 3 position 5, a second timer is actuated for measuring time required to press the centrally lit button. A third timer is actuated for measuring the time required to press the object button. The times required for the subject to perform the indicated operations (e.g., each individual process stop as well as the total combined process) are thereby measured and recorded in a procedure allowing measurement of a subject's physical ability, such as, for example, accuracy, speed, peripheral vision, dexterity, flexibility, range of motion, etc.

This method is applicable for various action utilizing, for example, the hands, feet, elbows, knees, and the like, so long as the appendage is capable of depressing a button or otherwise triggering a microswitch.

The hemispherical system is now described in more detail with reference now to FIG. 3A and B. The hemispherical reflex testing system 86 includes a housing 88 having a substantially hemispherical interior surface 90 including several dozen lighted button-actuated electrical switches 100.

The hemispherical system 86 is intended for use in therapeutic/diagnostic centers as well as athletic training facilities. Each lighted button 100 includes an annunciator light (e.g., an LED) and a sensor microswitch for generating a sensor input signal for transmission to a computer or controller 112 connected thereto. Typically, the lighted buttons 100 are arrayed in radial lines within the hemispherical surface 90. A first, large, lighted start/stop/reset button 114 is disposed approximately at the center of the hemisphere, at the intersection of two perpendicular lines bisecting the hemisphere. A first circular array 116 of twelve small, typically equally spaced lighted buttons 100 encircles the central lighted button 114 at a first radius.

The first circular array 116 of lighted buttons corresponds roughly to the positions of the numerals on an analog clock face. Six more circles of twelve lighted buttons each are arranged at radii progressively larger than the first radial array 116, thereby providing twelve linear, radially projecting lines of seven lighted buttons 100 each. The buttons 100 are spaced evenly in radius to the edge of the hemispherical interior surface 90.

Alternatively, the buttons in first circular array 116 can be irregularly spaced, and more or fewer than twelve buttons can be included, and the remaining buttons 100 may be in a curved (as opposed to straight) line or may be irregularly or randomly positioned about the hemispherical interior surface 90.

As discussed, the hemisphere surface 90 can be defined as four quadrants, the first quadrant 120 begins at position one (i.e., with the one o'clock radial array) and extends clockwise through position three (including three radial arrays of small buttons 100). The second quadrant 122 begins at position four and extends clockwise through position six (also including three radial arrays of small buttons 100). The third quadrant 124 begins at position seven and extends clockwise through position nine and the fourth quadrant 126 begins at position ten and extends clockwise through position twelve (corresponding to the vertically aligned buttons at twelve o'clock).

The four quadrants are arrayed to cover a 360° circle within the hemispherical surface 90. For purposes of nomenclature, button 132 is at position three, radius five, counting radially outwardly from center button 114.

In use, a subject stands or sits at a test position 130 (for example, designated positions for left and right feet) approximately the center of the hemisphere and positions, presses, or otherwise contacts an extremity (e.g., a hand) on the central lighted button 114, thereby activating the system and indicating that the user is ready to begin. A test or exercise pattern of light illumination is then commenced.

During the test, the user begins with the hands at rest and one of the smaller lighted buttons (e.g., 132 at radial row three, position five) is illuminated (thus becoming an 'object button'); the user immediately depresses the object button 132 and then reaches back to touch the central lighted button 114, thus indicating an end to a test move. The controller 112 includes a timer for measuring the time taken for each step.

In the example described, when the fifth reset light located on row position three is lit, the controller immediately actuates (e.g., turns on) a first timer, thus measuring time required for the user to press the object button 132. Immediately upon pressing button 132 (which is also deemed a reset button 132), a second timer is actuated for measuring time required to press the center reset button 114.

The times required for the user to perform the indicated operations are thereby measured and recorded in a procedure allowing measurement of a subject's accuracy, overall eye-to-hand coordination, speed and range of motion (e.g., for hands, feet, elbows, knees, and the like.) Differences in times measured for buttons at different heights and radii are useful for characterizing the user's range of motion and peripheral vision. As the distance across which the subject moved an object is know, an objective metric of physical and cognitive ability can be calculated.

Driving Reflex Device

Figure 4:
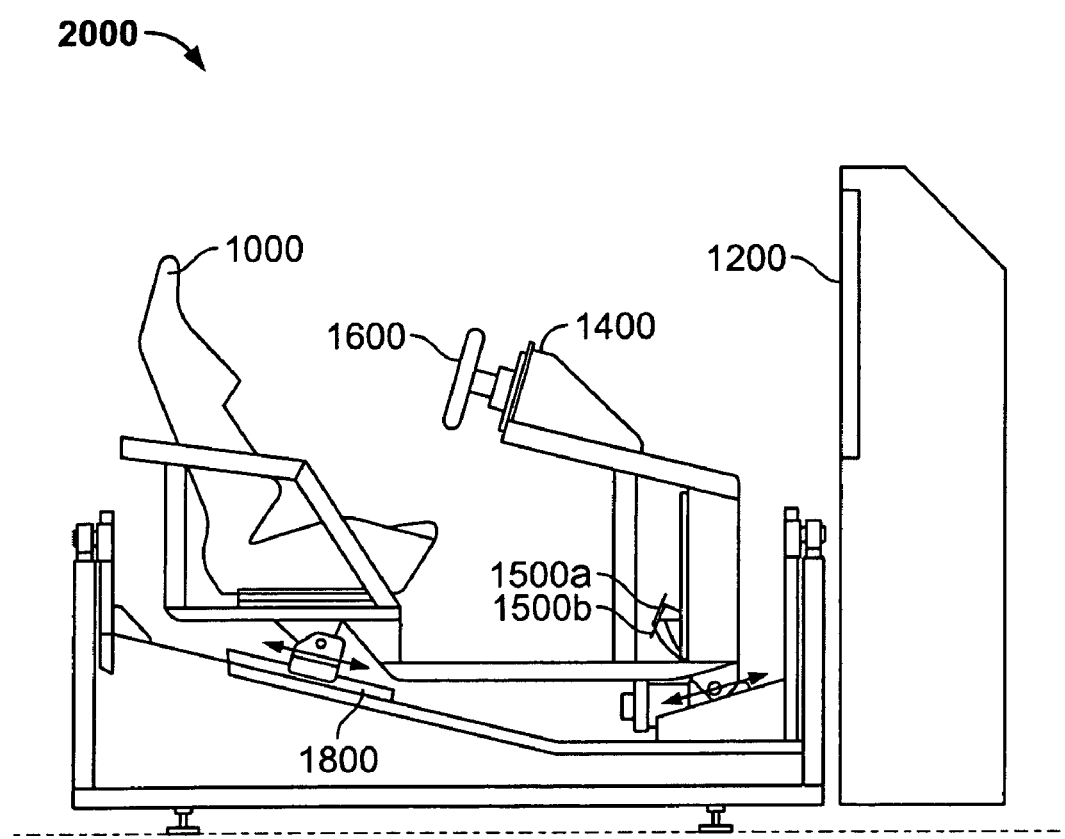
FIG. 4 is a diagram of a drawing reflex test device.

In another embodiment, a driving reflex device 2000 is provided, as shown in FIG. 4. The driving reflex device 2000 is schematically represented in FIG. 4. The driving reflex device 2000 comprises a driver's seat 1000 and a display monitor 1200 disposed at a forward portion of the driver's seat 1000 to display a forward image which is supposed to be viewed by the driver during a simulation drive.

The driver's seat 1000 is adjustable in height and can be moved forward or backward using adjustment device 1800. The driving reflex device further comprises an operation unit such as an accelerator pedal (or accelerator) 1500a which enables a driver to accelerate a virtual speed of the reflex machine, a brake pedal (or brake) 1500b which enables the driver to reduce the virtual running speed of the reflex machine, and a steering wheel 1600 as a direction changer. The driving console 1400 may also include a turn signal mechanism, light switch, speedometer and the like, consistent with controls found on a typical driving console. The console 1400 can also include devices such as speakers and mirrors for further simulating a driving environment.

The driving reflex device is used to measure response times for drivers and can be used to test drivers periodically during their driving life-time. The device is useful by, for example, a department of motor vehicles office, driver education, or insurance companies to test and/or train potential and existing drivers to obtain an objective measure of driving ability in order to determine the appropriateness of a driver's license.

For example, the driving reflex device can be used to measure the reflex times of a driver upon receiving his/her driver's license at which point the driver's reflex data can be stored as a base-line for that driver's driving ability compared to normative data. Subsequently (e.g., yearly) the driver is tested on the reflex driving device and the reflex timing recorded and compared. The data can be used to assess the ability of the driver and to restrict the driver's license accordingly.

In use, a driver sits on the seat 1000, holds the steering wheel 1600, pushes a start button to set the device to an ON-state, and steps on the accelerator 1500a. A computer then executes a driving scenario on the display monitor 1200. The scenario may include any number of annunciator actions including indicating that the driver should signal and turn left. For example, a stop light may turn red indicating that the driver should "stop". Upon visualizing or hearing the annunciator, the driver must respond appropriately.

The driving system comprises sensors that measure various control operations in response to the scenario being displayed. For example, the scenario may display a red-light signal thus instructing the driver to apply the brake pedal. The time period between the display of the red-light and the braking action are then measure and recorded. Any number of reactions and measurements can be made. For example, the speed at which that accelerator pedal is depressed, the speed at which the steering wheel is turned, and the like. Sensor and motion detection methods are known and are electronically coupled to the system using known techniques. In a further aspect, an audio device is also present to provide sounds associated with driving including, for example, a siren and horn.

A feature of the computer in the disclosure is that several sets of test results can be stored and date-stamped so that a technician, examiner, therapist or physician can analyze a subject's progress or change over time by analyzing the trends in reaction time for selected stimuli. The data can be organized by test type and by the specific stimulus presented to the subject.

The computer or controller includes software for analyzing and displaying the data in any of several formats. The data can be moved to a spreadsheet or database for storage, plotted and printed. The computer software allows a technician, therapist or physician to either perform a test (or exercise), archive subject histories, or display the subject histories, and prepare written documents, as necessary.

For example, an initial menu available on a computer can include one or more of the following, but typically will include all of the following: (a) test format selection; (b) test configuration; and (c) subject information. Once this information has been entered, the system is set in a ready condition whereby activation of the system begins the testing procedure. Once the test is performed, the system can display the results, record the results, and/or display the results with analysis.

The initial menu allows a technician, therapist examiner or physician an opportunity to record information needed to perform the test or exercise and provide identifying information about the subject such as the subject's name and other vital information. The therapist examiner also selects whether to use a random sequence of a selected length or a preselected sequence and whether results should be recorded (for a test) or not recorded (for an exercise).

Initially, the user or subject must be readied for the test whereby the hand or fingers are placed and checked and sensors are checked for activation and function. Once the appropriate sensors are activated, a waiting period of 1 to several second (e.g., approximately 10 seconds) may pass before the actual test begins. In performing the test, the software directs the system to activate a certain annunciator (e.g., a light). The system then records the time interval between the light coming on or instruction provided and the appropriate button being pressed or action performed.

In one aspect, different annunciators may be used. For example, optical, auditory, and tactile annunciators may be used. In one aspect, a first test sequence can use a visual annunciator (e.g., a light). Once the test sequence is completed using light annunciators, the test is repeated using the vibrotactile buzzer/vibrating or auditory annunciators. If an error occurs during testing (such as the wrong finger button being pressed) the error is recorded along with other test results.

One feature of controller 112 is that several sets of test results can be stored and date-stamped so that the therapist or physician can analyze a subject's progress over time by analyzing the trends in reaction time for selected stimuli. The data can be organized by test type and by the specific stimulus presented to the subject.

The computer or controller used in any of the four embodiments described above includes software for analyzing and displaying the data in any of several formats. The data can be moved to a spreadsheet or database for storage, plotted and printed. The computer software displays a menu allowing the therapist, technician or physician to either perform a test (or exercise), archive subject histories, or display the subject histories (e.g., on display monitor 136).

Figure 5:
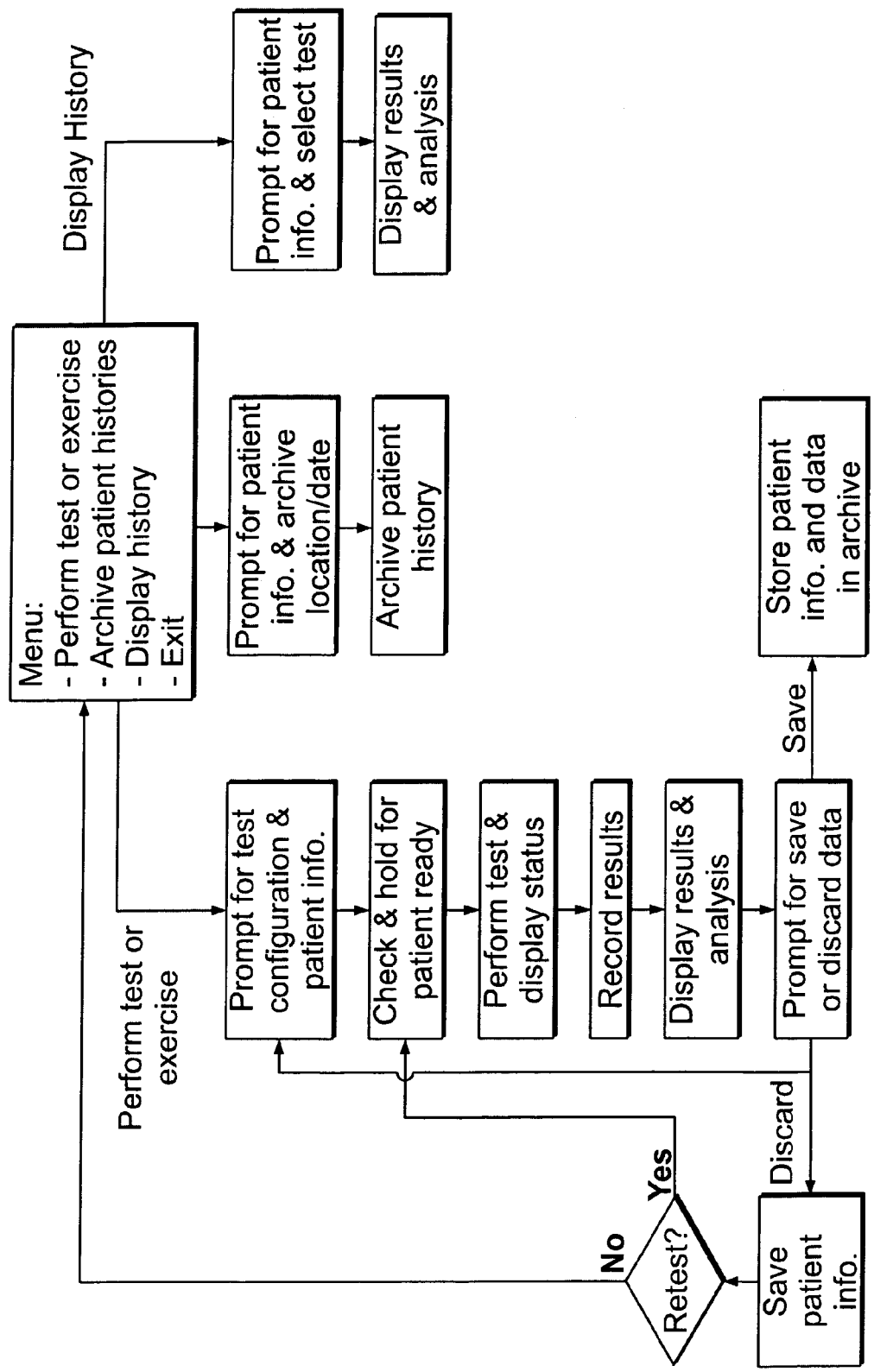
FIG. 5 is a software system flow diagram illustrating the conceptual phases of the operations performed during execution of the controller software.
Figure 6:
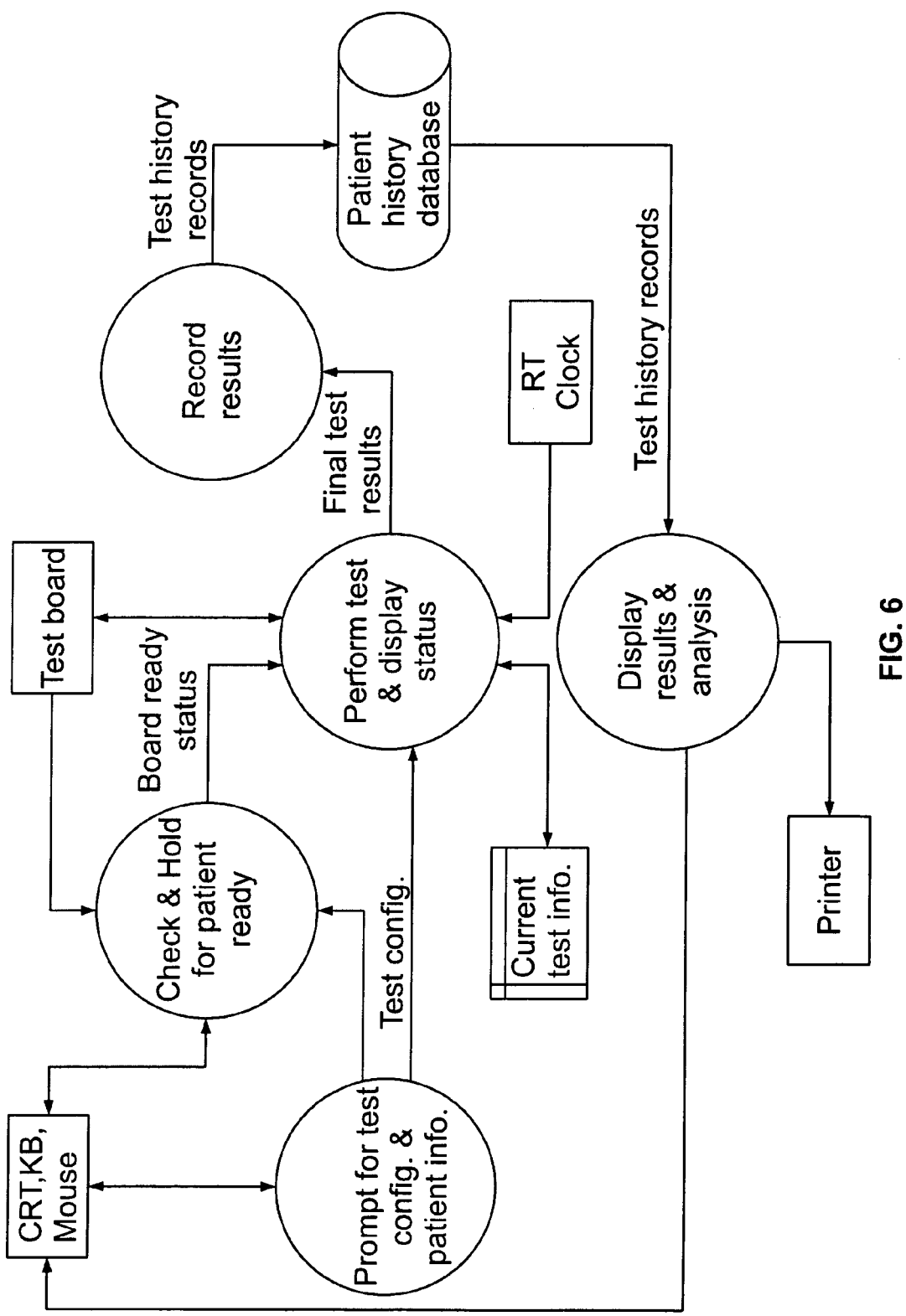
FIG. 6 is a controller software data flow diagram illustrating the flow and storage of information in the "performed test" sequence, the square boxes are external elements.
Figure 7:
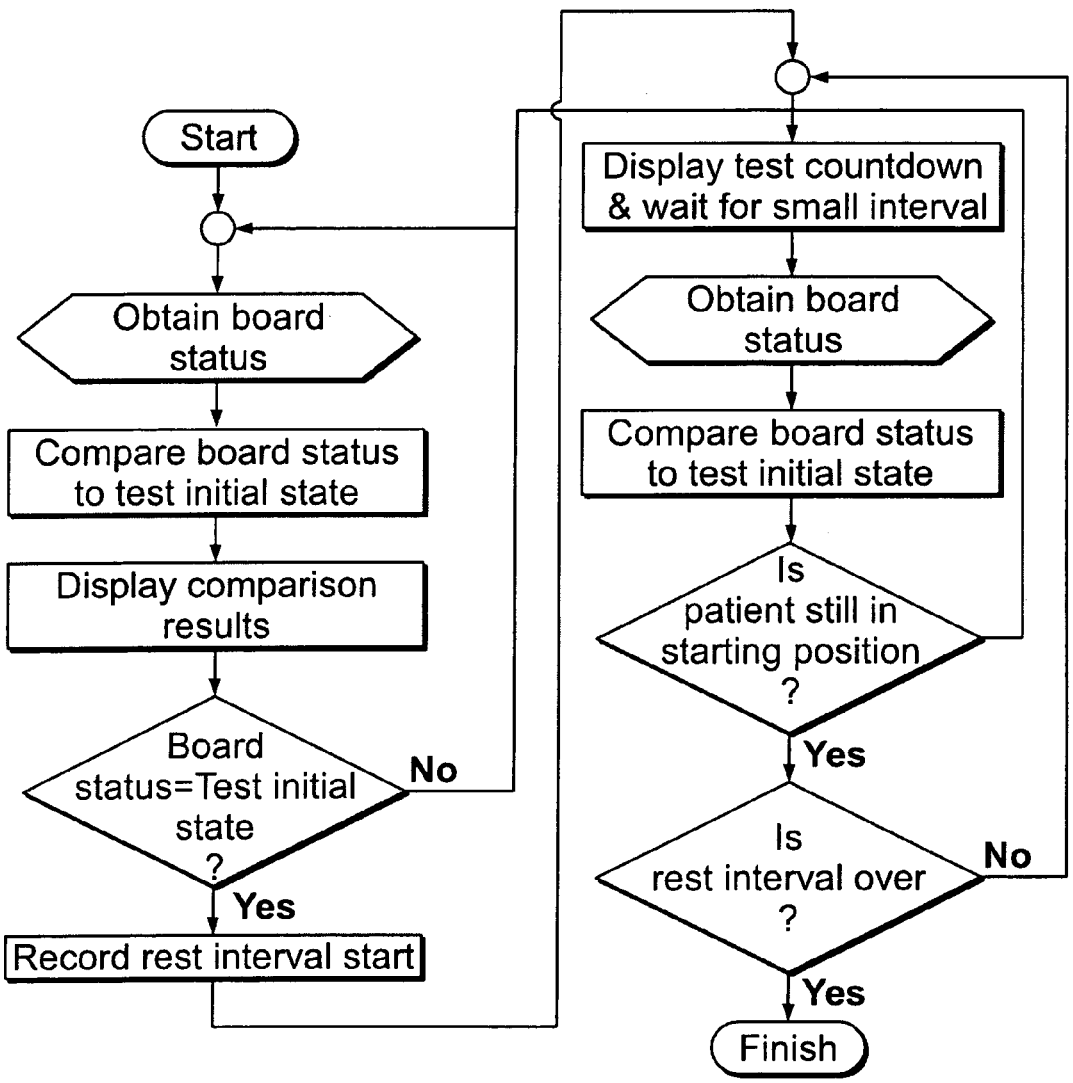
FIG. 7 is a software logic diagram for the "check and hold for patient ready" sequence of steps, as used in conjunction with the finger test system of FIG. 1.

FIG. 5 is a software system flow diagram illustrating the conceptual phases of the operations performed during execution of the controller software. If performing a test is chosen from an initial menu, the first step is to prompt for test configuration and subject information, then check and hold for subject ready condition, perform the test and display the results, record the results, and display the results with analysis.

The initial prompt gives the therapist an opportunity to record information needed to perform the test or exercise and provide identifying information about the subject such as the subject name and other vital information. The therapist also selects whether to use a random sequence of a selected length or a preselected sequence and whether results should be recorded (for a test) or not recorded (for an exercise).

The microswitch sensors used in the apparati disclosed herein are commercially available or easily fabricated by one of skill in the art. For example, reset button 32 in finger subarea 28a of the embodiment of FIG. 1 or, alternatively, a sensing microswitch incorporated into receiving aperture 67 of the peg-board embodiment of FIG. 2, or a sensing microswitch included in button 132 of the hemispherical test system of FIG. 3, or a microswitch electrically coupled to a brake pedal 1500b of FIG. 4 can be commercially available microswitches. The controller (e.g., 112) includes circuitry responsive to each sensing microswitch. The controller (e.g., 112) provides annunciator driving outputs to start each test and is responsive to flip-flop circuits to detect and time the passing of each tested event.

As described herein, the reflex measuring systems of the disclosure obtain data comprising reflex timing for various activities and associated with certain movements. The controller 112 can communicate full or compressed data to remote station(s) for interpretation by a medical professional or others or for storage at a central database. The communications network can be represents any packet-switched network such as a local area network or the Internet The controller 112 can be any computer suitable for use in order to implement or perform various embodiments of the invention. Such a computer includes a processor that in one embodiment belongs to the PENTIUM® family of microprocessors manufactured by the Intel Corporation of Santa Clara, Calif. However, the computer can be implemented on computers based upon other microprocessors, such as the MIPS® family of microprocessors from the Silicon Graphics Corporation, the POWERPC® family of microprocessors from both the Motorola Corporation and the IBM Corporation, the PRECISION ARCHITECTURE® family of microprocessors from the Hewlett-Packard Company, the SPARC® family of microprocessors from the Sun Microsystems Corporation, or the ALPHA® family of microprocessors from the Compaq Computer Corporation.

The computer includes system memory, including read only memory (ROM) and random access memory (RAM), which is connected to the processor by a system data/address bus. ROM represents any device that is primarily read-only including electrically erasable programmable read-only memory (EEPROM), flash memory, and the like. RAM represents any random access memory such as Synchronous Dynamic Random Access Memory.

Within the computer, the input/output bus is connected to the data/address bus via a bus controller. In one embodiment, the input/output bus is implemented as a standard Peripheral Component Interconnect (PCI) bus. The bus controller examines all signals from the processor to route the signals to the appropriate bus. Signals between the processor and the system memory are passed through the bus controller. However, signals from the processor intended for devices other than system memory are routed onto the input/output bus.

Various devices may be connected to the input/output bus including hard disk drives, disk drives, and optical drives, such as a CD-ROM drive. A video display or other display-type device is connected to the input/output bus via a video adapter. The computer also includes a modem and network interface for communicating over a network via either a wired or wireless connection.

From the description provided, it will be appreciated by those skilled in the art that the disclosure makes available a response measuring system for measuring the time required for a user or subject to respond to a prompting, annunciated event, including a controller with at least first and second annunciator driving outputs, first and second sensor input receiving circuits, a timer responsive to the annunciator driving outputs and the sensor input receivers and a memory responsive to the sensor input receivers. The response measuring system also includes a first annunciator responsive to the controller first annunciator driving output, a second annunciator responsive to the controller second annunciator driving output, a first sensor connected to a sensor input signal generator generating a first sensor input signal for transmission to the controller first sensor input receiver, a second sensor connected to a sensor input signal generator generating a second sensor input signal for transmission to the controller second sensor input receiver, a support member or housing carrying the first annunciator, the second annunciator, the first sensor and the second sensor; where the annunciators are positioned to be perceivable (e.g., seen, heard, or felt) by the user, and where the controller timer is configured to measure time elapsed between actuation of the first annunciator and generation of the first sensor input signal, and generate a response time signal from the elapsed time, and where the controller memory is configured to store and, optionally, display the elapsed time.

Of course, many trivial substitutions are possible, sensing micro-switches need not be used for sensing the position of a peg or depression by a user, thermal sensors, optical sensors, or capacitive sensors or pressure sensors may be employed, instead. Similarly, LEDs need not be used to provide visual prompting of the user, instead, incandescent bulbs, fluorescent lamps, plasma display elements or Liquid Crystal Display (LCD) display elements may be used to provide a visible annunciator to prompt the user.

In one aspect, the disclosure provides a method of diagnosing ailments such as neurological disorders, brain tumors, stroke, and the like. For example, a subject's response behavior can be measured and compared to a control behavioral response or normative data, as well as individual data. The control behavior response can be a response time for a specific task or a plurality of specific tasks. In one aspect an "experimental" measurement is compared to a previous "baseline" measurement of the subject. The comparison provides an object measurement of a change in the subject's response.

In another aspect, the disclosure provides a method of measuring dramatic changes in life such as Alzheimers, stroke, and the like. The methods of the disclosure provides an objective measure of how such ailments affect a subject's mental and physical performance. Such historical and current measurements of a subjects performance on the apparati of the disclosure provide evidence of deterioration of a conditions or improvement of a condition.

In yet another aspect, the objective measure of a subject's response can be combined with other neurological measurements such as, for example, MRI or CAT scan measurements. Such a combination of data provides important tools for physicians in the diagnosis of neurological diseases or disorders. For example, the information from the methods of the disclosure (e.g., a response profile) can be combined with MRI data showing a brain tumor to determine.

Various algorithms can be used to collate and analyze the reflex data and attribute the date to one or more medical ailments, diseases or disorders. For example, methods for using neural networks can be implement in the computer systems of the invention. A neural network typically possesses a three-layer structure comprising an input unit, intermediate unit, and output unit. In the learning process, one or more values are calculated from a plurality of reflex measurements, a pair of a certain measurements and a desirable output value based on that measurements are given to the network, and the network structure is decided. By giving a plurality of measurements to the network obtained in the learning, the output value can be obtained.

In the learning process, the combination weight value is adjusted so that the network output is brought closer to the desirable output value. Repeating the presentation of the measurements eventually allows the desired output to be displayed even when any measurement is given to the network. In this way, the brain function is determined by the measurements observed from the subject. In other words, using reflex measurements from a training set of individuals having known ailments, diseases or disorders, the reflex measurements of test subject can be used to diagnose similar ailments, diseases and disorders by comparing the test reflex measurements with known measurements.

In another aspect, fuzzy theory can be used to analyze the reflex measurements to predict ailments, diseases and disorders. For example, "short reflex times" or on the contrary, "long reflex times" can be used. When brain functions are examined, short reflex times will likely be attributed to proper neurological and motor functions. In the fuzzy theory, this kind of set is called the fuzzy set. The fuzzy sets are prepared in advance, and at the time of examination, brain and motor functions are determined by the indexes observed from the subject.

In yet a further aspect, the methods use expert systems. An expert system is a system provides the computer with the medical field theories and experimental knowledge which doctors, therapists and the like possess and allow the computer and reflex measurement system to go through accurate judgment and operation procedures. For example, in determining an ailment, disease or disorder, various conditions are given to each measurement or movement and the results when such conditions hold are set as experimental knowledge. At the time of examination, each measurement obtained from the subject is applied to the condition, respectively, and the ailment, disease or disorder is determined.

The methods of the disclosure provide data that can give the most up-to-date mental/physical status, for example, prior to surgery. This data can then be used for a variety of purposes including to compare with post-surgery results. In this method, a response profile is created as soon as possible after surgery to see if surgery was successful.

In another aspect, the method of the disclosure provides for the ability to track the progress of therapy, the baseline will help the doctors, therapists, subjects, and the families follow recovery after surgery.

The methods and systems of the disclosure provide a useful tool to show how a patient of subject performs mentally and physically after the stresses of surgery. For example, if a patient or subject has slower comprehension and movement, the system gives them hope by tracking and showing the slightest improvement unnoticeable by the human eye by the objective measurements of the system.

The methods and systems of the disclosure may also be used to track the effectiveness of medications on rehabilitating the mind and body by comparing how a patient or subject performs following administration of the medicine versus without (e.g., prior to) taking the medicine.

Where baseline measurements are not available for a specific subject, the subject can be compared to an average or normative subject, wherein the average subject is an average of data scores compiled on the system from control individuals.

The methods and system can help in determine the appropriate treatment or length of treatment for a subject. The methods and systems can provide a objective baseline upon which a treated patient or subject is measured. For example, measurements can be taken on any one or more of the apparati above before medicating the subject and an appropriate time after. If improvement is observed then the treatment regimen is maintained, but if no improvement is observed then the treatment can be modified or changed appropriately. Furthermore, the methods and systems provide physicians and therapists with information regards to type, length, and degree of prescribed treatments.

In another aspect, the methods and systems allow for proper management of workers receiving Workman's Compensation Benefits. In this aspect, an individual baseline on body movements and cognitive function is created for a worker upon employment (or alternatively an average baseline can be used), showing the ability to (i) identify stimulus, (ii) identify a response selection, and (iii) provide a response. This baseline can then be used to identify an injury thereby justifying benefits or to measure improvement in a subject receiving benefits. This aspect allows for settlement of employee cases with true objective data on a subject before injury, after injury, during recovery, and upon completion of treatment. Furthermore, the objective methods of the disclosure assist in identifying treatments that provide beneficial results and thus limits payments for treatments and medications that are working to resolve the injury. In addition, the methods and systems may be helpful to settle reopened cases based on each employee's comparative data.

In another aspect, the methods and systems of the disclosure may help to facilitate insight in to potential performance problems based on trends allowing for preventative measures before possible injuries. For example, using the driving system described herein, deterioration in reflexes in driving performance can be identified and preventative measures taken to avoid accidents by limiting or affecting the subject's driving abilities.

Additional uses of the methods and systems of the disclosure include:

(a) Use findings to support clinical data;

(b) Use findings to discount exaggerated or fabricated claims;

(c) Aid employees injured outside of work by providing baseline information, thereby keeping responsibility for rehabilitation on proper insurance carrier;

(d) Deter employees from filing a fraudulent claim (e) Create a baseline to show the level of cognitive and physical function (drug and aptitude tests exist to eliminate poor performers, but do not allow employer to see to what degree applicant can use their mind and body to react to life's random stimuli);

(f) Create baselines on existing employees and record any pre-existing injuries;

(g) Retest on a consistent basis to monitor employees' performance;

(h) Can show potential signs of loss in abilities to do job or effects job has on employee;

(i) Allows identification and treatment before a claim is filed;

(j) After injury—gives employer/employee proof of the extent of injury;

(k) Reduces treatment costs associated with ineffective treatments;

(j) Reduce the size of settlements (based on each employee's baseline and relation to recovery period);

(k) Reduce the number of claims (existing baseline data can deter filing false claims due to new tests showing inconsistent data);

(l) Prove whether there is an increase of injury in reopened cases during and after employment;

(m) Track effects of prescribed medications to determine ability to fulfill all job requirements;

(n) Test employees before they return to work after being injured either on or off the job (off job—in order to put responsibility on correct insurance carrier); and (o) Use as part of Exit-interview—to provide a most current baseline to compare if employee tries to file a valid/invalid claim after leaving employment.

EXAMPLE

Neurological injury often affects a person's motor function, and depending upon the type of injury, one or both limbs can be affected. Objective measures after neurological injury are critical for rehabilitative treatment planning. The automated pegboard system (APB 2000) depicted in FIG. 3 is a useful tool that objectively quantifies the temporal components involved with motor function. In the data presented below, the APB 2000 and the Wolf Motor Function Test (WMFT) data were compared to assess criterion validity.

Two groups of matched subjects participated in this study. Group 1 consisted of seven healthy adults (mean age of 67.40 years) while group 2 consisted of seven medically stable stroke survivors (man age 69.17 years). The APB 2000 test/retest interval was 2-weeks.

Subjects from the groups were prompted by the APB 2000 system to move specific pegs to specific new locations. The total time required for each stage of the process (e.g., comprehension, execution, and completion) were objectively measured, tracked and recorded. Each subject was positioned in a super-incumbent posture facing the mid-portion of the APB 2000. An APB 2000 thigh stabilization bar was positioned at the anterior aspect of the superior one-quarter of the subject's thigh. This location is determined by measuring the distance from the subject's anterior superior iliac spine to the floor and multiplied by 0.75. The APB 2000 pegboard angle of inclination was adjusted appropriately for each subject at increment gradients between 9° and 26°.

The subjects were explained the APB 2000 testing procedure. Once the subjects have adequate practice time with the APB 2000, formal testing was begun. The subject read and responded to a 21 sequence command on the monitor. Subjects were asked to move various shapes across their body to various locations on the pegboard. To begin the task the subject pressed the start/stop button on the APB 2000. At the end of the test sequence the same start/stop button was pressed to complete that test. Commands included, but were not limited to, using the left hand to move a rectangle from right column one to center column two (Right-to-Center test). The computer recorded each command, displayed time, distance, return time, and trip time per command. Retesting was performed 5-9 days following the initial test.

The single measure intraclass correlation coefficient (ICC) was 0.78 and 0.90 for the second and third trials, respectively. The average measure ICC was 0.93. The reliability of the APB 2000 exceeded the 0.90 value to establish reliability when using the average measure ICC.

A number of embodiments of the disclosure have been described. Nevertheless, it will be understood that various modifications may be made without departing from the spirit and scope of the disclosure. Accordingly, other embodiments are within the scope of the following claims.

What is claimed is:

1. A response measuring system for measuring the time required for a user to respond to an event, comprising:
   a computer;
   a display screen;
   a seat;
   a steering device;
   a start button for starting a diagnostic process, wherein actuation of the start button initiates the display of a first instruction to a user to perform a first driving-related cognitive task;
   an end button for terminating the diagnostic process;
   one or more foot pedals;
   a plurality of sensor input receivers associated with the steering device and the one or more foot pedals for sensing a change in position of the steering device and one or more foot pedals; and
   a computer readable medium comprising instructions to cause the display of a display scenario on the display screen, the display scenario comprising annunciator outputs;
   a first timer configured to measure a first elapsed time between actuation of the start button and initiation of a change in position of the steering device or a foot pedal indicative of completion of the first cognitive task;
   a second timer configured to measure a second elapsed time between completion of the first cognitive task and completion of a first physical task comprised of movement of the steering device or a foot pedal from a first, predetermined position to a second predetermined position, wherein the second controller timer begins measuring time upon completion of the first cognitive task;
   a third timer configured to measure a third elapsed time between completion of the first physical task and actuation of the end button, wherein the third controller timer begins measuring time upon completion of the first physical task; and
   a memory device to store at least one of the elapsed times.

2. The response measuring system of claim 1, further comprising a communication device for communicating data comprising user specific information and elapsed time information to a remote location.

3. The system of claim 1, further comprising a remote data storage device.

4. The system of claim 1, further comprising a database comprising user specific information.

5. The system of claim 4, wherein the elapsed time information is added to the database and associated with the user specific information.

6. The system of claim 1, wherein the user specific information includes medical information selected from the group consisting of age, weight, height, optical vision, hearing, body image information, injuries, and combinations thereof.

7. A reflex response device for diagnosing a neurological and/or musculoskeletal disease or disorder comprising:
   a controller comprising:
      a plurality of annunciator driving outputs;
      a plurality of sensor input receivers;
      first, second and third timers responsive to at least one of the said annunciator driving outputs and the sensor input receivers; and
   a memory responsive to said sensor input receivers;
   a start button for starting a diagnostic process, wherein actuation of the start button initiates the display of a first instruction to a user to perform a first cognitive task;
   an end button for terminating the diagnostic process;
   a plurality of annunciators responsive to said controller annunciator driving outputs;
   a plurality of sensors, each individually connected to a plurality of sensor input signal generators each generating a sensor input signal transmitted to said plurality sensor of input receivers;

wherein each of the plurality of annunciators are positioned to be perceivable by the user and wherein each of the sensors are operable by the user;

said first controller timer being configured to measure a first elapsed time between actuation of the start button and generation of a corresponding input from a first sensor indicative of completion of the first cognitive task;

said second controller timer being configured to measure a second elapsed time between completion of the first cognitive task and completion of a first physical task, wherein the second controller timer begins measuring time upon completion of the first cognitive task;

said third controller timer being configured to measure a third elapsed time between completion of the first physical task and actuation of the end button, wherein the third controller timer begins measuring time upon completion of the first physical task;

wherein the memory is configured to store the first, second and third elapsed times;

a database comprising user specific information; and a computer program on computer readable medium comprising instructions to cause the computer to acquire an elapsed time and to associate the elapsed time with the user specific information to diagnose a neurological and/or a musculoskeletal disease or disorder based upon the elapsed lime.

8. The reflex device of claim 7, wherein the computer program comprises a neural network, fuzzy logic, and/or expert system.

9. The reflex device of claim 7, wherein the device comprises a housing configured as a partial spherical interior surface, wherein the annunciators and sensors are arranged on the partial spherical interior surface.

10. The reflex device of claim 7, wherein the database comprises information related to magnetic resonance imaging (MRI), cat-scan data, medication information, surgical information, and combinations thereof.

11. The reflex device of claim 7, wherein the device comprises:
   a display screen;
   a seat;
   a steering device;
   one or more foot pedals;
   wherein the plurality of sensor input receivers are associated with the steering device and the one or more foot pedals for sensing a change in position of the steering device and one or more foot pedals.

12. The reflex device of claim 7, wherein the device comprises a hand location support, wherein the plurality of annunciators and corresponding sensors are associated with each finger of the hand location support.

13. The reflex device of claim 7, wherein the device comprises:
   the controller, including first and second annunciator driving outputs, first and second sensor input receivers, the timer responsive to the annunciator driving outputs and the sensor input receivers and the memory responsive to said sensor input receivers;
   the first annunciator responsive to the controller first annunciator driving output;
   the second annunciator responsive to the controller second annunciator driving output;
   the first sensor connected to the sensor input signal generator generating the first sensor input signal transmitted to the controller first sensor input receiver;
   the second sensor connected to the sensor input signal generator generating a second sensor input signal transmitted to the controller second sensor input receiver;
   a support member carrying the first annunciator, the second annunciator, the first sensor and the second sensor, wherein the annunciators are positioned to be perceivable by the user;
   the controller timer being configured to measure time elapsed between actuation of the first annunciator and generation of the first sensor input signal, and generate a response time signal from the elapsed time;
   wherein the memory is configured to store the elapsed time; and
   wherein the support member includes a housing with a first area configured to receive a first hand with fingers and thumb pressed against the first area.

14. The response measuring system of claim 13, wherein the support member includes a housing with a second area configured to receive a second hand opposite said first hand, with fingers and thumb pressed against the second area.

15. The response measuring system of claim 7, wherein the device comprises,
   the controller including first and second annunciator driving outputs, first and second sensor input receivers; the timer responsive to the annunciator driving outputs and the sensor input receivers and a memory responsive to the sensor input receivers;
   the first annunciator responsive to the controller first annunciator driving output;
   the second annunciator responsive to the controller second annunciator driving output;
   the first sensor connected to the sensor input signal generator generating the first sensor input signal transmitted to the controller first sensor input receiver;
   the second sensor connected to the sensor input signal generator generating the second sensor input signal transmitted to the controller second sensor input receiver;
   a support member carrying the first annunciator, the second annunciator, the first sensor and the second sensor, wherein the annunciators are positioned to be perceivable by the user;
   the controller timer being configured to measure time elapsed between actuation of the first annunciator and generation of the first sensor input signal, and generate the response time signal from the elapsed time;
   wherein the memory is configured to store the elapsed time;
   wherein the support member includes a housing configured as a partial spherical interior surface;
   the annunciators and sensors being arranged on the partial spherical interior surface.

16. The response measuring system of claim 15, further including a central actuator button including a third sensor connected to a sensor input signal generator generating a third sensor input signal transmitted to the controller third sensor input receiver;
   the central actuator button being disposed in the center of the substantially hemispherical interior surface;
   the first annunciator and the first sensor being incorporated into a first lighted press button incorporating an electrical switch; the second annunciator and the second sensor being incorporated into a second lighted press button incorporating an electrical switch; and
   the first and second lighted press buttons being disposed on the substantially hemispherical interior surface: the controller timer being configured to measure time elapsed between actuation of the first annunciator and generation of the third sensor input signal, and generate a response time signal from said elapsed time.

17. The response measuring system of claim 16, wherein the central actuator button, the first lighted press button and the second lighted press button are disposed in a linear array aligned along a radial line within said substantially hemispherical interior surface.

18. The response measuring system of claim 17, further comprising third and fourth lighted press buttons disposed in a second linear array aligned along a second radial line within the substantially hemispherical interior surface and radially spaced from the first and second lighted press buttons.

19. The response measuring system of claim 15, the substantially hemispherical interior surface including a test position proximate the center of the hemisphere at a bottom edge; and being situated to facilitate use by a standing or sitting user.

20. The response measuring system of claim 19, the substantially hemispherical interior surface test position including designated positions for left and right feet disposed directly in front of the central actuator button.

* * * * *